United States Patent [19]
Yokoi

[11] Patent Number: 4,763,662
[45] Date of Patent: Aug. 16, 1988

[54] ULTRASONIC BIOPSY ENDOSCOPE WITH EXTENSIBLE GUIDE SHEATH

[75] Inventor: Takeshi Yokoi, Tokyo, Japan

[73] Assignee: Olympus Optical Co., Ltd., Tokyo, Japan

[21] Appl. No.: 868,304

[22] Filed: May 27, 1986

[30] Foreign Application Priority Data

Jun. 7, 1985 [JP] Japan ................................ 60-123598
Sep. 28, 1985 [JP] Japan ................................ 60-216049

[51] Int. Cl.$^4$ ............................................. A61B 10/00
[52] U.S. Cl. ......................................... 128/660; 128/4
[58] Field of Search ............................... 128/660–663, 128/4–6

[56] References Cited

U.S. PATENT DOCUMENTS

| | | | |
|---|---|---|---|
| 4,178,920 | 12/1979 | Cawood, Jr. et al. | 128/4 |
| 4,245,624 | 1/1981 | Komiya | 128/772 X |
| 4,327,738 | 5/1982 | Green et al. | 128/660 |
| 4,346,717 | 8/1982 | Haerten | 128/660 |
| 4,368,642 | 1/1983 | Carodiskey . | |
| 4,401,123 | 8/1983 | Baba | 128/660 |
| 4,582,067 | 4/1986 | Silverstein et al. | 128/663 |
| 4,586,491 | 5/1986 | Carpenter | 128/6 |
| 4,605,009 | 8/1986 | Pourcelot et al. | 128/6 X |

FOREIGN PATENT DOCUMENTS

3241178 10/1984 Fed. Rep. of Germany ...... 128/660
1311292 10/1961 France ................................ 128/660

OTHER PUBLICATIONS

Ultrasonic Tomography by Means of an Ultrasonic Fiberendoscope (W. D. Strom et al), Endoscopy 12 (1980), 241-244.

Primary Examiner—Francis J. Jaworski
Attorney, Agent, or Firm—Frishauf, Holtz, Goodman & Woodward

[57] ABSTRACT

An ultrasonic diagnostic apparatus includes an operation section and an insertion section adapted to be inserted into the body cavity of a human being. The insertion section has an insertion channel extending therethrough. A guide sheath is slidably inserted into the channel and has a distal end portion pivotally supported on the distal end of the insertion section by link arms. An ultrasonic probe is fixed to the distal end of the insertion section. An image guide extends through the sheath to the end face thereof. A guide channel for guiding a puncture needle extends through the sheath and opens at the end face thereof. When being pushed out from the insertion section the distal end portion of the sheath is pivoted to change its direction.

16 Claims, 6 Drawing Sheets

ULTRASONIC BIOPSY ENDOSCOPE WITH EXTENSIBLE GUIDE SHEATH

BACKGROUND OF THE INVENTION

This invention relates to an ultrasonic diagnostic apparatus and in particular an ultrasonic diagnostic apparatus adapted to insert an ultrasonic wave scanner into the body cavity of a human subject to permit an ultrasonic diagnosis to be made from within the body cavity.

Recently an ultrasonic diagnostic apparatus is provided which is designed to insert an ultrasonic wave scanner into the body cavity of a human being and to apply the scanner directly to a region of interest (lesion) for diagnosis. This type of diagnostic apparatus can obtain a high-resolution cross-sectional image in comparison with that obtained by ultrasonically diagnosing the lesion from outside the human subject. The lesion of the human subject is penetrated by a puncture needle, while being examined. A high-resolution cross-sectional image assures a safer and more positive needle penetration for puncture.

Where the diseased part of the body is to be punctured, not only the high-frequency diagnostic apparatus but also an endoscope is inserted within the body cavity and puncture needle is guided into the diseased part through the endoscope. However, if the high-frequency diagnostic apparatus and endoscope are both inserted into the body cavity, then much pain is inflicted on the patient. Furthermore, it is difficult to insert and withdraw these apparatuses into and out of the body cavity.

If during the insertion of the apparatus or penetration of the puncture needle the region of interest can be visually observed, then it is possible to perform a positive operation.

SUMMARY OF THE INVENTION

It is accordingly the object of this invention to provide a high-frequency diagnostic apparatus which can readily be inserted into or withdrawn from the body cavity of a patient and can provide a visual observation on a region of interest of a patient and/or perform various treatments for that region.

In order to obtain the aforementioned object there is provided an ultrasonic diagnostic apparatus, comprising: an operation section; a flexible insertion section extending from the operation section and adapted to be inserted into the body cavity of a human being, said insertion section including an insertion channel which extends through the insertion section and has one end opening to the distal end of the insertion section and the other end communicating with the operation section; an ultrasonic scanner having ultrasonic wave oscillation means attached to the distal end of the insertion section and emitting an ultrasonic wave toward a predetermined scanning range to permit a region of interest within the body cavity to be observed by the ultrasonic wave; a guide sheath slidably inserted into the insertion channel and having a distal end portion extending from the distal end of the insertion section and a distal end face located in a position intersecting an axis of the insertion section; and a support mechanism pivotally supporting the distal end portion of the guide sheath on the distal end portion of the insertion section; wherein the distal end portion of the guide sheath is moved, during the withdrawal of the guide sheath back into the insertion section, to a position where it is snugly received on the distal end portion of the insertion section and, during the pushing out of the guide sheath from the insertion section, is rotated around the support mechanism to change its direction.

BRIEF DESCRIPTION OF THE DRAWINGS

FIGS. 1 to 5 show an ultrasonic diagnostic apparatus according to a first embodiment of this invention; in which FIG. 1 is a front view showing a whole of the apparatus, FIG. 2 is a perspective view showing a distal end portion of an insertion section, FIG. 3 is a side view showing the distal end portion of the insertion section, FIG. 4 is a sectional view showing the distal end portion of the insertion section as inserted into the human stomach, and FIG. 5 is a partly expanded sectional view showing a guide sheath;

FIGS. 8 and 9 show an ultrasonic diagnostic apparatus according to a fourth embodiment of this invention, in which FIG. 8 is a perspective view showing a distal end portion of an insertion section thereof and FIG. 9 is a sectional view showing the distal end portion of the insertion section which is shown in a different operative state from that in FIG. 9;

DETAILED DESCRIPTION OF THE PREFERRED EMBODIMENTS

The embodiments of this invention will be explained in detail with reference to the accompanying drawings.

Figure 1:
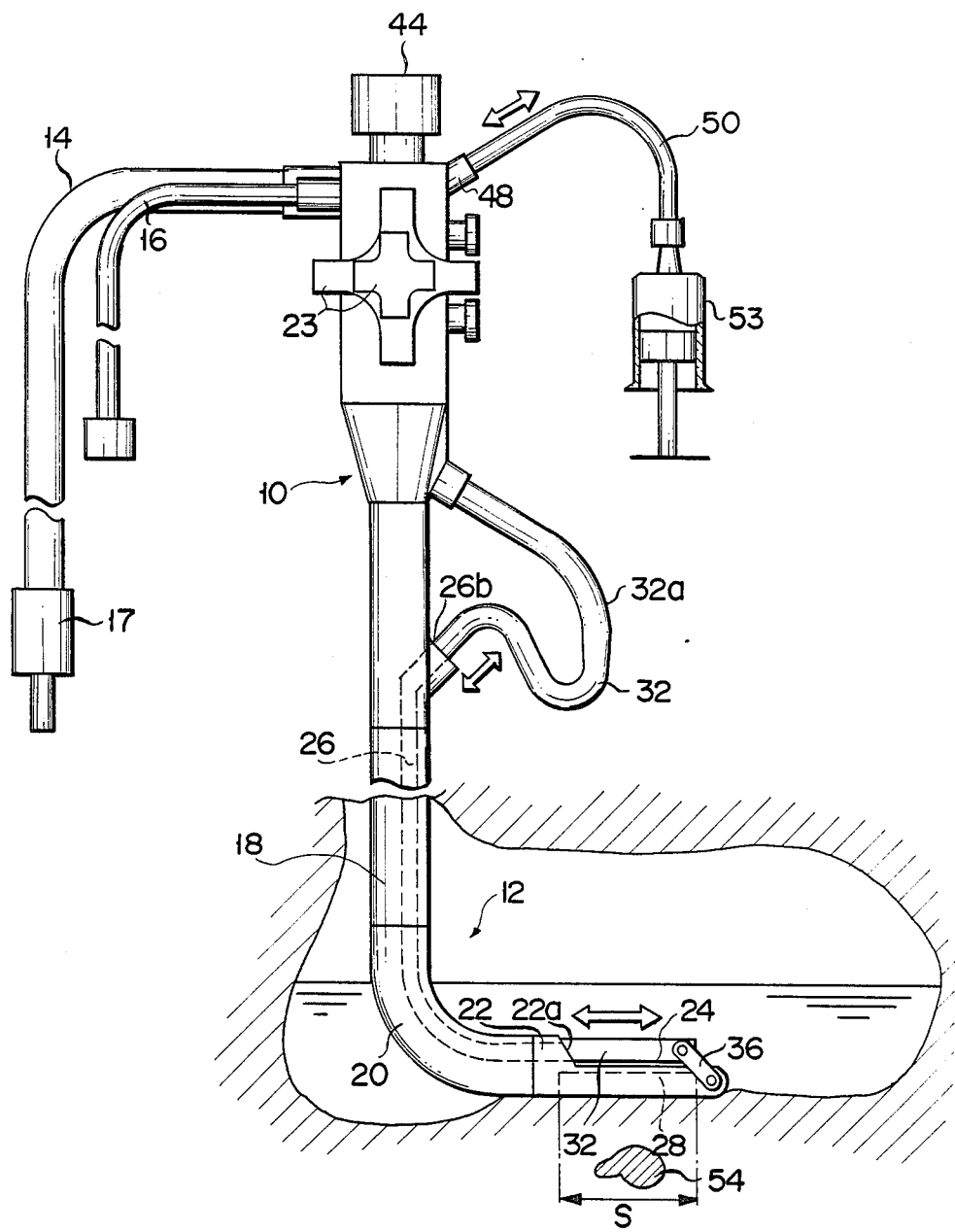
Figure 2:
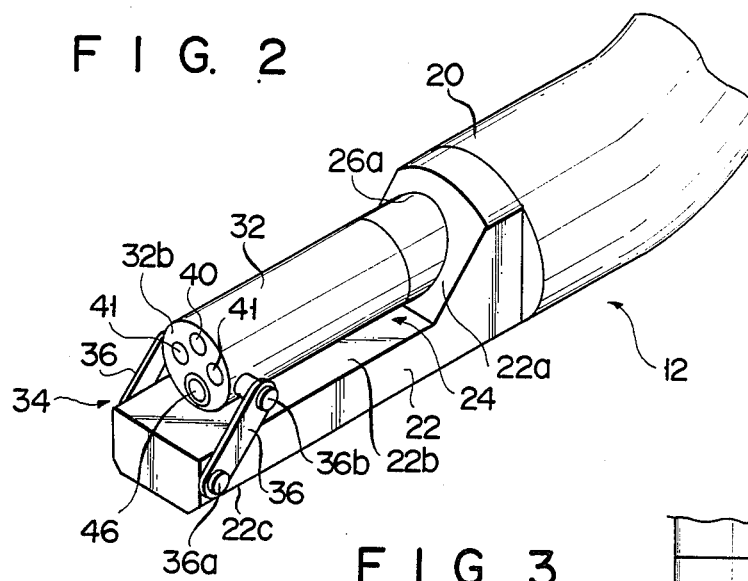
Figure 3:
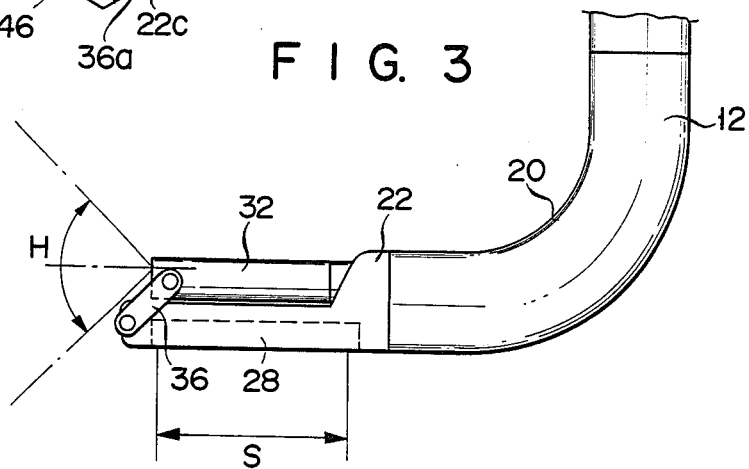
Figure 4:
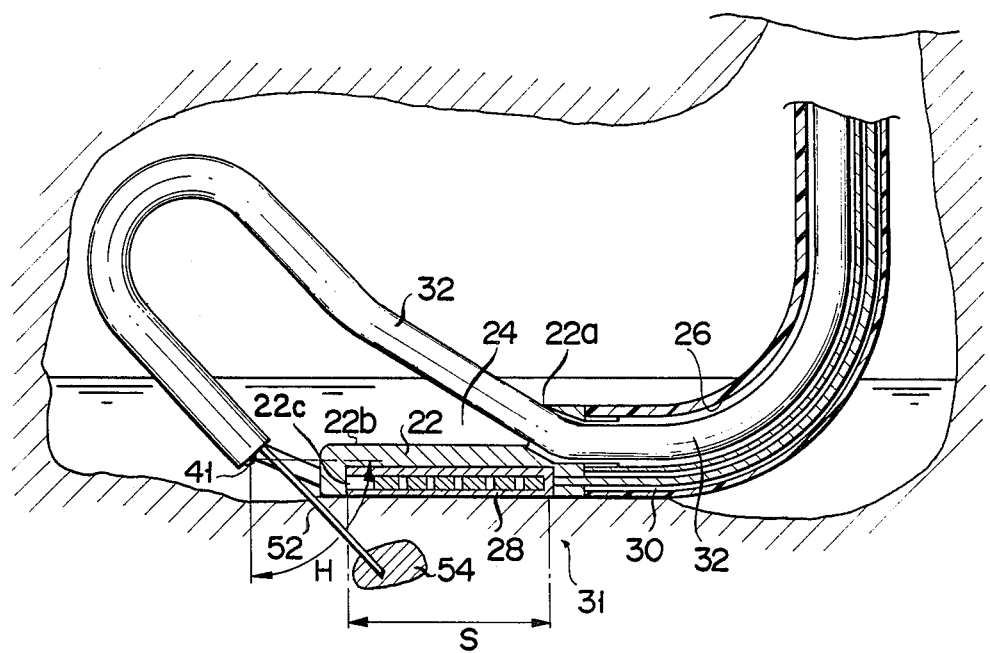

FIGS. 1 to 5 show an ultrasonic diagnostic apparatus according to a first embodiment of this invention. As shown in FIG. 1, the diagnostic apparatus includes operation section 10 and tubular insertion section 12 extending from the operation section and adapted to be inserted into the body cavity. Universal cord 14 and electrical cable 16 extend from operation section 10. Connector 17 is mounted on the extended end of universal cord 14. This connector is to be connected to a light source device (not shown). Electric cable 16 is connected to an ultrasonic observation apparatus (not shown). Insertion section 12 has flexible portion 18 extending from operation section 10, bend portion 20 extending from the distal end of the flexible portion, and a rigid, distal end member 22 fixed to the end of the bend portion. Portion 22 is remotely bent by actuating operation knob 23 mounted on operation section 10. Distal end member 22 has a longitudinal cross-section of a substantially L-shaped configuration and includes inclined surface 22a extending in a direction intersecting an axis of insertion section 12, upper surface 22b continued to the inclined surface 22a and extending along the axial direction of the insertion section, and bottom surface 22c located opposite to upper surface 22b. Receiving section 24 is defined by inclined surface 22a and upper surface 22b to receive a distal end portion of a guide sheath as set forth below. Insertion channel 26 is formed within insertion section 12 such that it extends along the axial direction of insertion section 12. Insertion channel 26 communicates at one end with outlet 26a opened at inclined surface 22a of distal end member 22 and at the other end with inlet 26b opened to the outside of operation section 10. As shown in FIG. 4, ultrasonic probe 28 is embedded in the bottom (22c) of distal end member 22 and has a scanning range S. Ultrasonic probe 28 is connected to electric cable 16 through signal line 30 which extends through insertion section 12 and operation section 10. Ultrasonic probe 28 and electric cable 30 constitute ultrasonic scanner 31.

Flexible guide sheath 32 is inserted into insertion channel 26 such that it can be moved back and forth. The distal end portion of guide sheath 32 extends out from outlet 26a of end member 22 and is received on receiving section 24. With the distal end portion of guide sheath 32 received on receiving section 24, the outer diameter of this assembly is so set that it does not exceed the diameter of the insertion section. The intermediate portion of guide sheath 32 is led out of insertion section 12 from outlet 26b, while being described in a substantially loop-like fashion, and again inserted into operation section 10. The loop-like portion of guide sheath 32 provides slide operation portion 32a. The distal end portion of sheath 32 is pivotally supported by support mechanism 34 on end member 22. Support mechanism 34 has a pair of parallel link arms 36, each of which is pivotally supported at one end on the distal end of the side surface of end member 22 by link pin 36a and at the other end on the outer periphery of the forward end portion of sheath 32 by link pin 36b. With guide sheath 32 fully receded, the distal end portion of the guide sheath is received on receiving section 24 as shown in FIGS. 1 to 3. When the guide sheath is moved forward to cause its distal end portion to be pushed out through the opening 26a, then the distal end portion of the guide sheath is swung as indicated in FIG. 4, causing distal end face 32b to vary in its direction.

Figure 5:
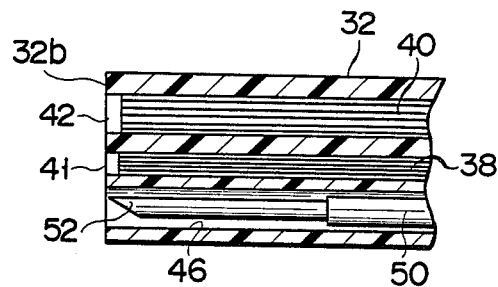

As shown in FIG. 5, a pair of light guides 38 and image guide 40, all made of optical fibers, are inserted into guide sheath 32. The distal ends of light guides 38 are optically coupled to lenses 41 attached to end face 32b of sheath 32 and the proximal ends of the respective light guides extend up to connector 17 through operation section 10 and universal cord 14. The distal end of image guide 40 is optically coupled to objective lens 42 which is fixed to end face 32b of guide sheath 32 and the proximal end of image guide 40 extends, through operation section 10, up to eyepiece section 44 on the operation section. Image guide 40 permits an optical image which is formed through objective lens 42 on the distal end face of the image guide to be transmitted to eyepiece section 44. Puncture needle guide channel 46 is formed within guide sheath 32. The distal end of channel 46 is opened at end face 32b of guide sheath 32 and the proximal end of channel 46 is connected through operation section 10 to insertion inlet 48 provided outside of the operation section. As shown in FIGS. 1 and 5, puncture tube 50 is inserted into guide channel 46 through insertion inlet 48. Puncture needle 52 is attached to the distal end of tube 52 so that it can be extended from the distal end, i.e., end face 32b of guide sheath 32. Syringe 53 (FIG. 1) is attached to the forward end of tube 50. An air-removing liquid-injecting channel, not shown, is formed within insertion section 12 to permit air-removing liquid to be injected through the channel into the body cavity.

The operation of the ultrasonic diagnostic apparatus so constructed will be explained.

Where the body cavity is to be diagnosed by the ultrasonic diagnostic apparatus, connector 17 of universal cord 14 is connected to the light source device and electric cable 16 is connected to the ultrasonic observation apparatus. Then, insertion section 12 is inserted into the body cavity. In this case, the distal end portion of guide sheath 32 is snugly received on receiving section 24 of end member 22 by withdrawing the guide sheath at the location of slide operation section 32a. When insertion section 12 is inserted into the body cavity, the distal end portion of guide sheath 32 is brought into intimate contact with upper surface 22b of end member 22. In this case, end face 32b of the sheath is located perpendicular to the axis of insertion section 12 to face toward the insertion direction. The light source device is driven with the result that light is emitted into the body cavity from the distal end of light guide 38, i.e., end face 32b of guide sheath 32 and thus a visual field H of the ultrasonic diagnostic apparatus is defined in front of end face 32b in the direction of the insertion of guide sheath 32.

Insertion section 12 is inserted, under a visual observation through image guide 40 and eyepiece section 44, into a wider spacing within the cavity, for example, a stomach. Upon the ultrasonic diagnosis, guide sheath 32 is forwardly pushed at the location of slide operation section 32a. As a result, the distal end portion of sheath 32 is advanced away from receiving section 24 under a pivotal movement of link arms 36, and rotated around guide pins 36a, 36b, while maintaining a predetermined distance relative to end member 22. The distal end portion of guide sheath 32 is pushed out from outlet 26a of end member 22 to provide a loop-like curved portion. As a result, end face 32b and visual field range H is oriented toward the scanning area S of ultrasonic probe 28.

Then the outer surface of ultrasonic probe 28, i.e., bottom surface of end member 22 is brought, under the visual observation through eyepiece 44, into contact with the body wall and an ultrasonic wave is emitted from the ultrasonic probe toward that region. Diseased part 54 can be spotted by observing an ultrasonic cross-sectional image within the scanning area S by virtue of the ultrasonic diagnostic apparatus.

After diseased part 54 is located, tube 50 with puncture needle 52 fixed at its distal end is inserted through inlet 48 into guide channel 46 of guide sheath 32. Needle 52 is projected from the forward end of guide sheath 32, and penetrated into part 54, while observing part 54 with the ultrasonic wave. The puncture angle of needle 52 is controlled by adjusting an amount of push into guide sheath 32 to control the pivotal movement of the distal end portion of the sheath. In this state, the syringe is operated to permit a liquid medicine, etc. to be ejected into diseased part 54 through tube 50 and needle 52 or to permit mucus, etc. to be sucked from part 54.

In the ultrasonic diagnostic apparatus so constructed, guide sheath 32 is inserted through insertion section 12 and the distal end portion of sheath 32 can be moved between the received position where the distal end portion is closely contact with end member 22 and an any arbitrary rotated position. Guide sheath 32 is equipped with an illumination optical system and observation optical system, as well as with puncture needle guide channel 46. For this reason, with the pivotal movement effected at the distal end portion of the guide sheath, the puncture needle is inserted through the guide channel into the body cavity so that it can be penetrated into the diseased part. It is therefore unnecessary to insert a separate endoscope into the body cavity as in the prior art, because the ultrasonic diagnostic apparatus of this invention serves that purpose. Furthermore, according to this invention it is possible to insert the insertion section into the body cavity with the distal end portion of the guide sheath snugly received on the distal end member. As a result, at the time of ultrasonic diagnosis and needle penetration the apparatus can readily be inserted in and withdrawn out of the body cavity without inflicting pain upon a patient.

The visual field range can be freely set by adjusting an amount of push of the guide sheath to change the direction in which the distal end portion of the guide sheath is oriented. It is therefore possible to visually observe the front area of the body cavity during the insertion of the insertion section into the body cavity as well as the ultrasonically scanned region of interest during the diagnosis by the ultrasonic wave and needle penetration.

Figure 6:
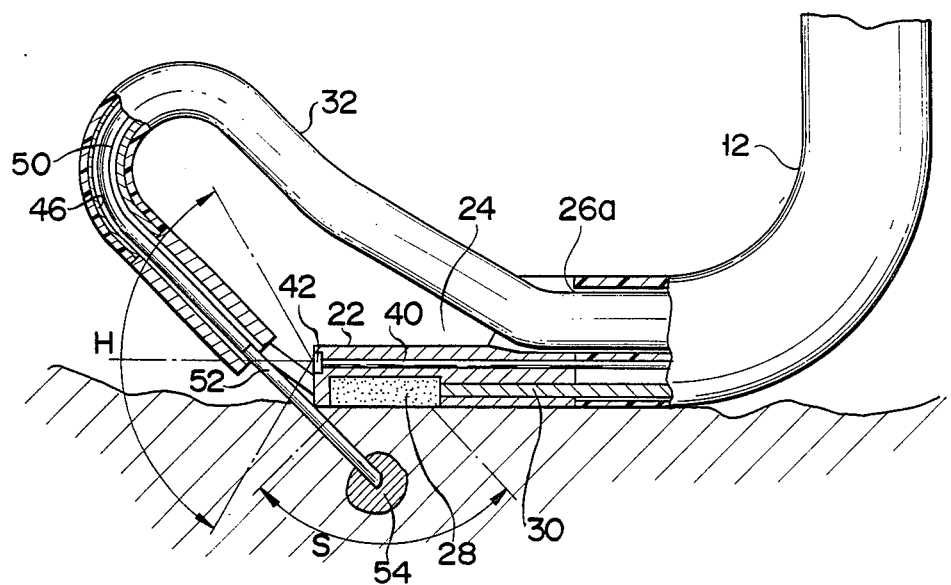
FIG. 6 is a sectional view, corresponding to FIG. 4, showing an ultrasonic diagnostic apparatus according to a second embodiment of this invention.

FIG. 6 shows a distal end portion of an ultrasonic diagnostic apparatus according to a second embodiment of this invention.

According to the second embodiment, only a puncture needle guide channel 46 is provided within guide sheath 32, and optical systems for illumination and observation are provided on the side of insertion section 12. That is, the light guide, not shown, and image guide 40 extend through insertion section 12 and distal end member 22, respectively, and one end of the light guide extends up to a connector of the aforementioned universal cord. Image guide 40 is connected, at one end, to eyepiece 44 and at the other end to objective lens 42 which is attached to the distal end face of end member 22. Similarly, the light guide is connected at the other end to a lens attached to the end face of the end member. The visual field range H is set at such a position as to permit, when puncture needle 52 is extended from the end face of guide sheath 32, its amount of extension to be visually viewed. The other arrangement of the second embodiment is similar to that of the first embodiment. Further explanation is therefore omitted.

Since according to the second embodiment no optical systems for illumination and observation are provided within guide sheath 32, it is possible to decrease the diameter of the sheath and thus the diameter of the insertion section as a whole.

Figure 7:
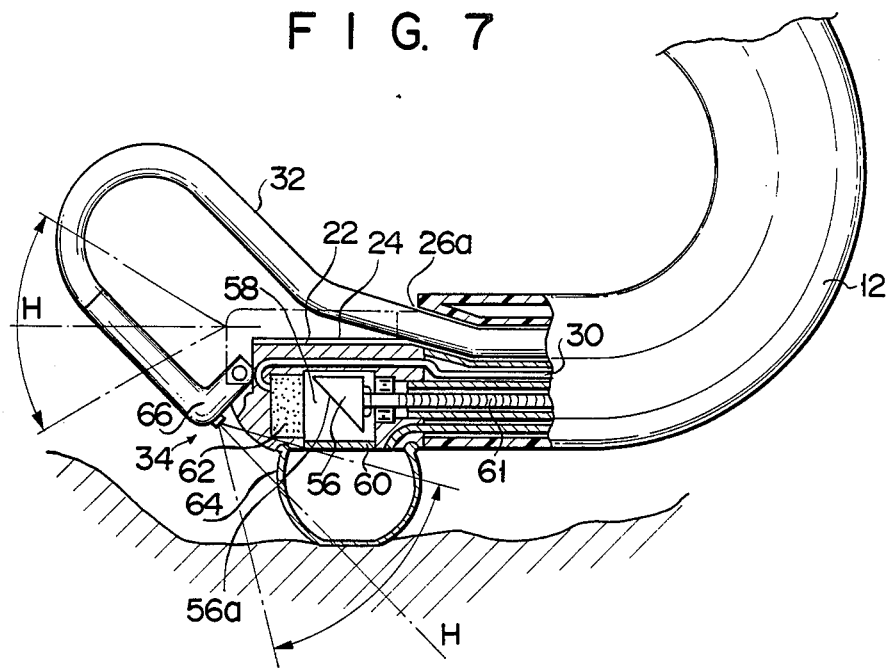
FIG. 7 is a sectional view, corresponding to FIG. 4, showing an ultrasonic diagnostic apparatus according to a third embodiment of this invention.

FIG. 7 shows a detail of the distal end section of an ultrasonic diagnostic apparatus according to a third embodiment of this invention. The third embodiment is different from the first embodiment in that the puncture needle guide channel is removed from guide sheath 32 and that, as an ultrasonic diagnostic system, use is made of a mechanical scanning system utilizing a rotation reflection member 56.

That is, receiving chamber 58 is formed in end member 22 and open to the bottom of the end member. The opening of the chamber is closed by ultrasonic emitting window 60. Rotation reflection member 56 is placed within chamber 58 and is connected to rotating shaft 61 extending into chamber 58 through insertion section 12. Shaft 61 is connected to driving means provided at operation section 10. Single probe 62 is placed within chamber 58 and connected through signal line 30 to electric cable 16 (see FIG. 1). Reflection member 56 has reflection face 56a which faces probe 62. Reflection face 56 reflects an ultrasonic wave, which is emitted from probe 62, and directs it toward the wall of the body cavity through window 60. The wave reflected on the wall of the body cavity is directed toward the probe by reflection face 56a. The outer surface of window 60 is covered by a balloon 64 which is fixed to forward end member 22. A transmission medium for an ultrasonic wave, such as a saline solution, is filled within balloon 64 and receiving chamber 58.

According to this embodiment, support mechanism 34 for pivotally supporting the distal end portion of guide sheath 32 has a pair of support arms 66 integral with the guide sheath. The respective arm 66 extends from the distal end of sheath 32 perpendicular to the axis of sheath 32. The extended end arm 66 is pivotally supported on end member 22.

According to the third embodiment, when guide sheath 32 is moved back and forth to permit the distal end portion of the sheath to be rotated, the visual field range H of the optical system for observation can be freely oriented in any direction. As a result, the insertion operation of insertion section 12, as well as an ultrasonic diagnosis, can be positively performed under a visual observation. Furthermore, since the distal end portion of the guide sheath is rotated around only one pivotal center, a stable pivotal operation can be obtained.

Figure 8:
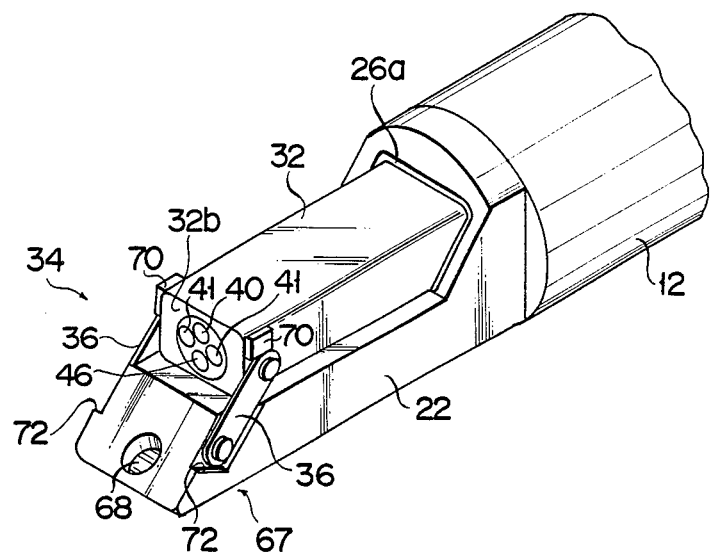
Figure 9:
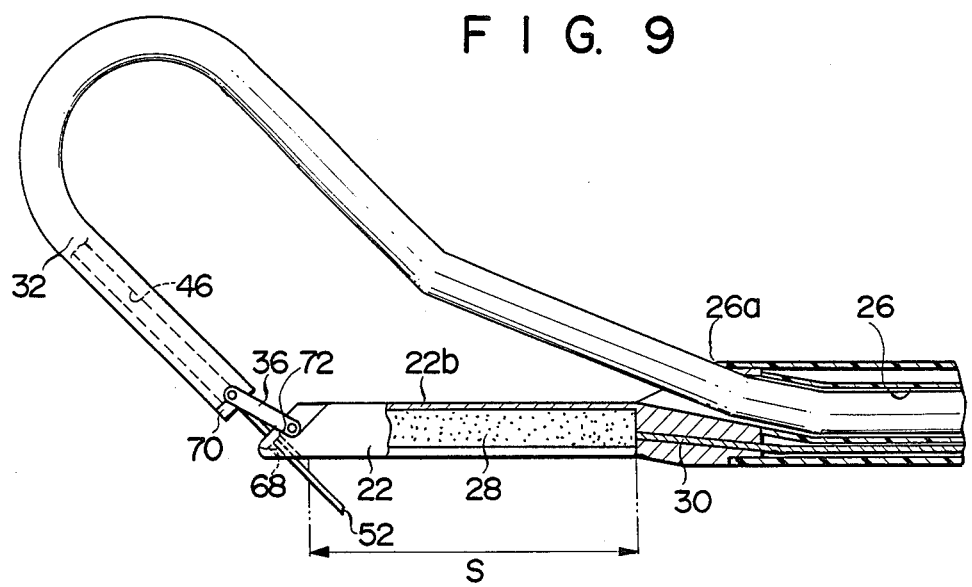

FIGS. 8 and 9 show an ultrasonic diagnostic apparatus according to a fourth embodiment of this invention.

The fourth embodiment is different from the first embodiment in that restricting means 67 is provided to restrict an amount of pivotal movement of the distal end portion of guide sheath 32 and that end member 22 has guide hole 68 for the puncture needle.

Guide hole 68 is diagonally formed with respect to the axis of insertion section 12 so that a central axis of guide hole 68 extends into the scanning area S of ultrasonic probe 26. Restricting means 67 has a pair of projections 70 formed on the distal end portion of guide sheath 32 to restrict an amount of pivotal movement of the distal end portion of the sheath relative to link arms 36 and a pair of stopper faces 72 formed on end member 22 to restrict an amount of pivotal movement of the link arms relative to the end member. When the distal end portion of guide sheath 32 is moved from a first position where it is located on receiving section 24 of end member 22 to a second position where the distal end portion of puncture needle guide channel 46 is located concentric with guide hole 68, i.e., end face 32b of guide sheath 32 confronts the scanning area S, then projections 70 and stopper faces 72 are brought into contact with the corresponding link arms 36 to prevent further pivotal movement of the distal end portion of the guide sheath. With the distal end portion of guide sheath 32 rotated to the second position, the tube for puncture is inserted into guide channel 46 and then puncture needle 52 fixed on the distal end of the tube is projected from end face 32b of the sheath into guide hole 68 so that it can be penetrated into the wall of the body cavity while being guided by the guide hole.

The aforementioned fourth embodiment offers, in addition to the advantages of the first embodiment, the following advantage.

The distal end portion of guide sheath 32 can always be moved to a predetermined position by regulating means 67. For this reason, puncture needle 52 can be projected always in a predetermined direction, thereby being readily inserted into guide hole 68. Since, at the time of the needle penetration, needle 52 is guided by guide hole 68, even if an external force acts upon the needle or guide sheath 32, the needle does not cause damage to the wall of the body cavity due to its vibration.

Figure 10:
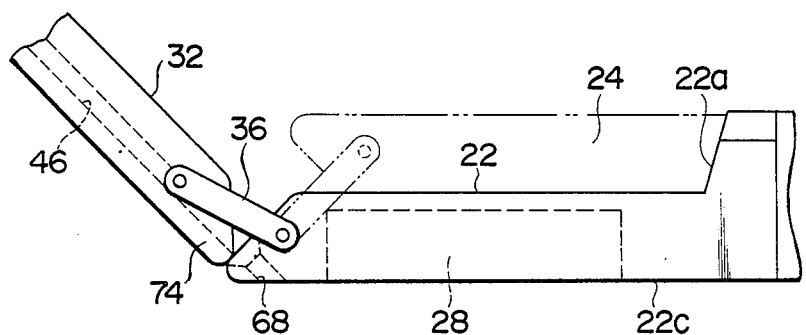
FIG. 10 shows a side view showing a distal end portion of an insertion section of an ultrasonic diagnostic apparatus according to a fifth embodiment of this invention.

FIG. 10 shows a fifth embodiment of this invention. The fifth embodiment is different from the fourth embodiment in the arrangement of restricting means 67.

According to the fifth embodiment, restricting means 67 has stopper section 74 formed at the distal end of guide sheath 32. When the distal end portion of guide sheath 32 is moved to a position where puncture needle guide channel 46 is located concentric with guide hole 68, stopper section 74 abuts against the end of end member 22 to prevent further rotation of the sheath. According to the fourth embodiment, simple restricting means is obtained in comparison with the fourth embodiment.

Figure 11:
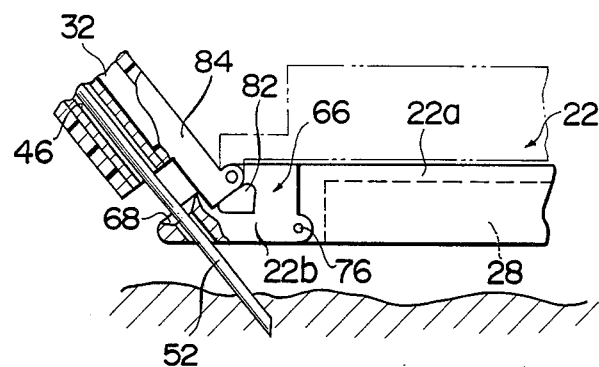
FIGS. 11 and 12 are side views showing a distal end portion of an insertion section of an ultrasonic diagnostic apparatus according to a sixth embodiment as used in different operative states.
Figure 12:
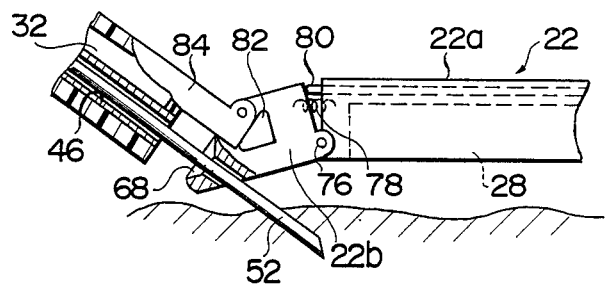

FIGS. 11 and 12 show a sixth embodiment of this invention. The sixth embodiment is different from the fourth embodiment with respect to restricting means 67 and end member 22.

That is, end member 22 is separated into first section 22a to which ultrasonic probe 28 is attached and second portion 22b having guide hole 68. Second section 22b is pivotally attached by pin 76 to first section 22a. Compression spring 78 is disposed between first section 22a and second section 22b to urge the second section into intimate contact with the first section. Slide rod 80 slidably extends through insertion section 12. The distal end of slide rod 80 abuts against second section 22b and the proximal end of slide rod 80 extends up to operation section 10 (FIG. 1). When slide rod 80 is pushed via operation section 10 to push second section 22b ahead, then the second section is pivotally moved counterclockwise against the urging force of spring 78.

Restricting means 67 has stopper 82 formed on second section 22b. The distal end of guide sheath 32 is pivotally supported on second section 22b through a pair of support arms 84 formed integral with the guide sheath. When, as shown in FIG. 12, the distal end portion is pivotally moved to a second position where puncture needle guide channel 46 is located concentric with guide hole 68, then support arm 84 abuts against stopper 82 to prevent further pivotal movement of the guide sheath.

According to the aforementioned sixth embodiment, if the distal end of guide sheath 32 is rotated to the second position and slide rod 80 is pushed ahead with puncture needle 52 inserted into guide hole 68, then second section 22b, guide sheath 32 and puncture needle 52 are rotated as one unit. Thus, the penetration direction of needle 52 can readily been varied by adjusting an amount of push into slide rod 80.

Figure 13:
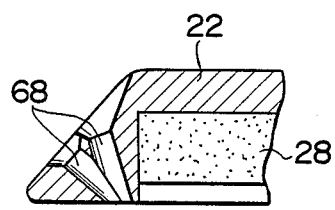
FIG. 13 is a sectional view showing a distal end portion of an insertion section of an ultrasonic diagnostic apparatus according to a seventh embodiment of this invention.

This invention is not limited to the above embodiments, and various changes and modifications can be effected therein by one skilled in the art without departing from the scope of the invention. In the embodiments of FIGS. 8 to 11, for example, a plurality of guide holes, for example, two may be formed at distal end member 22 as shown in FIG. 13.

What is claimed is:

1. An ultrasonic diagnostic apparatus, comprising:
   an operation section;
   a flexible insertion section extending from said operation section and adapted to be inserted into the body cavity of a human being, said insertion section including an insertion channel which extends through the insertion section and has one end open to a distal end of the insertion section and the other end communicating with said operation section, said insertion section having a longitudinal axis at said distal end;
   an ultrasonic scanner having an ultrasonic wave oscillation means and attached to a side of the distal end of said insertion section for emitting ultrasonic waves toward, and receiving said waves from, a region of interest within the body for observation thereof, said ultrasonic wave oscillation means being oriented to emit said waves in a scan plane extending laterally with respect to said longitudinal axis, said ultrasonic scanner having a back side oriented towards said longitudinal axis;
   a guide sheath slidably inserted into said insertion channel and having a distal end portion adapted for sliding between housed and extended positions; and
   a support means for pivotally supporting the distal end portion of said guide sheath on the distal end portion of said insertion section and for moving the distal end portion of said guide sheath, during withdrawal of said guide sheath back into said insertion section, to said housed position where it is located at the back side of the ultrasonic scanner in the distal end portion of the insertion section and exposed to the outside of the distal end portion of the insertion section and, during the pushing out of the guide sheath from said insertion section to said extended position, for moving the distal end portion of said guide sheath in a pivotal operation around the support means to change its direction;
   wherein the distal end portion of the guide sheath, in its extended position, has a distal end face oriented such that a direction line normal to said end face intersects said scan plane.

2. An ultrasonic diagnostic apparatus according to claim 1, which further comprises an observation optical system disposed in said guide sheath and having one end extending up to the end face of said guide sheath and the other end extending up to said operation section, said observation optical system having a visual field range corresponding to a direction in which the distal end portion of the guide sheath is oriented.

3. An ultrasonic diagnostic apparatus according to claim 2, wherein said observation optical system has an objective lens attached to said distal end face of said guide sheath, eyepiece section provided at said operation section, and an optical fiber having one end connected to said objective lens and the other end connected to said eyepiece section.

4. An ultrasonic diagnostic apparatus according to claim 2, wherein said guide sheath has a guide channel extending therethrough and having one end opened at said distal end face of said guide sheath and the other end extending up to said operation section, and which further comprises a puncture tube slidably inserted into the guide channel and a puncture needle attached to the distal end of said puncture tube to be extendible from the distal end face of said guide sheath.

5. An ultrasonic diagnostic apparatus according to claim 1, wherein said guide sheath has a guide channel extending through the guide sheath, said guide channel having one end opened at the distal end face of said guide sheath and the other end extending up to said operation section, and which further comprises a puncture tube slidably inserted into said guide channel, and a puncture needle attached to the distal end of said puncture tube to be extendible from the distal end face of said guide sheath.

6. An ultrasonic diagnostic apparatus according to claim 5, wherein said insertion section has means for defining a guide hole for guiding said puncture needle, said guide hole being formed at the distal end of said insertion section so as to direct the puncture tube toward the scanning range of said ultrasonic wave oscillation means.

7. An ultrasonic diagnostic apparatus according to claim 6, which further comprises restricting means, when the distal end portion of said guide sheath is moved from said housed position to a rotated position where said guide channel within said distal end portion of said guide sheath is located concentric with said guide hole, for restricting further movement of the distal end portion of said guide sheath.

8. An ultrasonic diagnostic apparatus according to claim 7, wherein said support mechanism has a pair of parallel link arms, one end of each link arm being pivotally attached to the distal end portion of said guide sheath and the other end thereof being pivotally attached to the distal end portion of said insertion section, and said restricting means includes a first stopper formed on the distal end portion of said guide sheath to restrict an amount of pivotal movement of the distal end portion of said guide sheath relative to said link arms and a second stopper formed on the distal end portion of said insertion section to restrict an amount of pivotal movement of the link arms relative to said insertion section.

9. An ultrasonic diagnostic apparatus according to claim 7, wherein said support mechanism has a pair of support arms, one end of each support arm being fixed to the distal end portion of said guide sheath and the other end thereof being pivotally supported on the distal end portion of said insertion section, and said restricting means includes a pair of stoppers formed on the distal end portion of said insertion section to abut against said support arms when said distal end portion of said guide sheath is moved to said rotated position.

10. An ultrasonic diagnostic apparatus according to claim 7, wherein said restricting means has a stopper formed on the distal end of said guide sheath to abut against the distal end of said insertion section when the distal end portion of said guide sheath is moved to said rotated position.

11. An ultrasonic diagnostic apparatus according to claim 6, wherein said distal end portion of said insertion section has a first section in which said ultrasonic wave oscillation means is provided and a second section on which said distal end portion of said guide sheath is supported and in which said guide hole is formed, said second section being pivotally supported by the first section, and which further comprises urging means for urging said second section into alignment with said first section and pushing means provided within said insertion section, for pushing said second section to pivot it against the urging force of said urging means.

12. An ultrasonic diagnostic apparatus according to claim 1, wherein said ultrasonic wave oscillation means has an ultrasonic probe fixed to said distal end portion of said insertion section.

13. An ultrasonic diagnostic apparatus according to claim 1, wherein said ultrasonic wave oscillation means has an ultrasonic probe provided within the distal end portion of said insertion section and a rotation reflection member rotatably mounted within the distal end portion of said insertion section, for reflecting ultrasonic wave emitted from the ultrasonic probe to direct it toward a region of interest within the body to be diagnosed.

14. An ultrasonic diagnostic apparatus according to claim 1, wherein said support means includes a pair of parallel link arms, one end of each link arm being pivotally attached to the distal end portion of the guide sheath and the other end thereof being pivotally attached to the distal end portion of the insertion section.

15. An ultrasonic diagnostic apparatus according to claim 1, wherein said distal end portion of the insertion section includes a receiving section located at the back side of the ultrasonic scanner and open to the outside of the distal end portion of the insertion section, for receiving the distal end portion of the guide sheath in the housed position.

16. An ultrasonic diagnostic apparatus according to claim 1, wherein said distal end portion of the insertion section includes a bottom surface opposite to the receiving section, and the ultrasonic scanner is embedded in the bottom surface.

* * * * *